(12) United States Patent
Geng et al.

(10) Patent No.: US 8,835,403 B2
(45) Date of Patent: Sep. 16, 2014

(54) ALGIN OLIGOSACCHARIDES AND THE DERIVATIVES THEREOF AS WELL AS THE MANUFACTURE AND THE USE OF THE SAME

(76) Inventors: Meiyu Geng, Qingdao (CN); Huashi Guan, Qingdao (CN); Xianliang Xin, Qingdao (CN); Zhao Yang, Qingdao (CN); Guangqiang Sun, Qingdao (CN)

( * ) Notice: Subject to any disclaimer, the term of this patent is extended or adjusted under 35 U.S.C. 154(b) by 627 days.

(21) Appl. No.: 10/594,100

(22) PCT Filed: Feb. 25, 2005

(86) PCT No.: PCT/CN2005/000226
§ 371 (c)(1),
(2), (4) Date: Jun. 29, 2007

(87) PCT Pub. No.: WO2005/089776
PCT Pub. Date: Sep. 29, 2005

(65) Prior Publication Data
US 2007/0254848 A1 Nov. 1, 2007

(30) Foreign Application Priority Data
Mar. 24, 2004 (CN) .......................... 2004 1 0023827

(51) Int. Cl.
| | | |
|---|---|---|
| A61K 31/7016 | (2006.01) | |
| A61K 31/702 | (2006.01) | |
| A61K 31/734 | (2006.01) | |
| A61P 25/28 | (2006.01) | |
| C07H 3/04 | (2006.01) | |
| C07H 3/06 | (2006.01) | |
| C08B 37/04 | (2006.01) | |
| C08B 37/00 | (2006.01) | |
| A61P 5/50 | (2006.01) | |

(52) U.S. Cl.
CPC .............. *C08B 37/0084* (2013.01); *C07H 3/06* (2013.01); *C07H 3/04* (2013.01); *C08B 37/0024* (2013.01)
USPC . 514/53; 514/54; 514/61; 536/3; 536/123.12; 536/124

(58) Field of Classification Search
None
See application file for complete search history.

(56) References Cited

U.S. PATENT DOCUMENTS

| 5,460,945 | A | 10/1995 | Springer et al. |
|---|---|---|---|
| 5,516,666 | A | 5/1996 | Nozomi et al. |
| 6,436,389 | B1 | 8/2002 | Gage et al. |
| 2002/0016453 | A1* | 2/2002 | Marritt .......................... 536/123 |

FOREIGN PATENT DOCUMENTS

| CN | 1341664 | 3/2002 |
|---|---|---|
| CN | 1341665 | 3/2002 |
| CN | 1380342 | 11/2002 |
| CN | 1401786 | 3/2003 |
| CN | 1408360 | 4/2003 |
| CN | 1414002 | 4/2003 |
| CN | 1454992 | 11/2003 |
| CN | 1473836 | 2/2004 |
| CN | 1486988 | 4/2004 |
| CN | 1562050 | 1/2005 |
| JP | 2002-047302 | 2/2002 |
| JP | 2003-521573 | 7/2003 |
| WO | 01/56404 | 8/2001 |

OTHER PUBLICATIONS

Yang, Z. et al "Preparation and characterization of oligomannuronates . . . " Carbohyd. Polym. (2004) vol. 58, pp. 115-121.*
Davies, M. et al "Prevention of type 2 diabetes . . . " Diabetic Med. (2004) vol. 21, pp. 403-414.*
Skyler, J. et al "Effects of oral insulin . . . " Diabetes Care (2005) vol. 28, No. 5, pp. 1068-1076.*
Hamilton, J. et al "Metformin as adjunct therapy . . . " (2003) vol. 26, No. 1, pp. 138-143.*
Doraiswamy, P. et al "Pharmacological strategies for the prevention of Alzheimer's disease" (2006) vol. 7, No. 1, pp. 1-10.*
Biessels, G. et al "Risk of dementia in diabetes mellitus . . . " Lancet Neurol. (2006) vol. 5, pp. 64-74.*
Clark, A. et al "Pancreatic islet amyloid and diabetes" Protein Reviews (2007) vol. 6, part 3, pp. 199-216.*
Marchesi, V. "Alzheimer's dementia begins as a disease of small blood vessels . . . " Faseb J. (2011) vol. 25, pp. 5-13.*
Machine translation of CN 1408360 (2003).*
Mesh definition of "oligosaccharide" retrieved May 21, 2012 http://www.nlm.nih.gov/cgi/mesh/2012/MB_cgi?mode=&index=9431&field=all&HM=&II=&PA=&form=&input=.*

(Continued)

*Primary Examiner* — Leigh Maier
(74) *Attorney, Agent, or Firm* — McCarter & English, LLP; Steven G. Davis; Wei Song

(57) ABSTRACT

The present invention provides an alginate oligosaccharide and its derivatives with the degree of polymerization ranging from 2 to 22. The alginate oligosaccharide is composed of β-D-mannuronic acid linked by 1,4 glycosidic bonds. The derivatives with the reduced terminal in position 1 of carboxyl radical can be prepared by oxidative degradation. The present invention also provides a process for preparing the alginate oligosaccharide and its derivatives, which includes the procedures that an alginate solution is reacted for 2 to 6 h in an autoclave at pH 2-6 and the temperature of 100-120° C., and pH is adjusted to 7 after the reaction is stopped, after which the resultant oligosaccharide is oxidized in the presence of an oxidant to obtain an oxidative degradation product. The alginate oligosaccharide and its derivatives of the invention can be used in the manufacture of a medicament for the prophylaxis and treatment of AD and diabetes.

10 Claims, 9 Drawing Sheets

(56) References Cited

OTHER PUBLICATIONS

Translation of Chinese application CN 01107952.5 (2002).*
International Search Report International Application No. PCT/CN2005/000226 dated May 19, 2005.
De Haas et al., "A synthetic lipopolysaccharide-binding peptide based on amino acids 27-39 of serum amyloid P component inhibits lipopolysaccharide-induced responses in human blood," J. Immunol., 1998, vol. 161, pp. 3607-3615.
Leca et al., "Expression of VCAM-1 (CD106) by a subset of TCRγδ—bearing lymphocyte clones," J. Immunol., 1995, vol. 154, pp. 1069-1077.
Rogers et al., "Epitope mapping of the Syrian hamster prion protein utilizing chimeric and mutant genes in a vaccinia virus expression system," J. Immunol., 1991, vol. 147, pp. 3568-3574.

* cited by examiner

ALGIN OLIGOSACCHARIDES AND THE DERIVATIVES THEREOF AS WELL AS THE MANUFACTURE AND THE USE OF THE SAME

TECHNICAL FIELD

The present invention relates to an alginate oligosaccharide and its derivatives, the preparation thereof, and the uses of the same in the treatment of Alzheimer's disease (AD) and diabetes.

BACKGROUND ART

AD and diabetes are currently common and frequently-occurring diseases which seriously endanger the health of human beings. Particularly, their incidence is increasing with the growth of the population of the old. So the prophylaxis and treatment of these diseases become more and more critical.

Current preventive and curative drugs for AD are unlikely to revolutionize the treatment of AD due to their limitation of the mere symptomatic relief or severe adverse effects. The drugs commonly used for diabetes are mainly insulin and other orally hypoglycemic drugs, most of which are disadvantageous in inconveniency for use and toxicity. Particularly, there are actually no effective drugs for type 2 diabetes. It has been found that the occurrence of AD and type 2 diabetes is related to the deposition of amyloid-beta (Aβ) and amylin (IAAP) the subsequently fibrillogenesis and increased free oxidative radicals, which gives rise to the fact that inhibition of the fibril formation of amyloid-beta and amylin becomes the perspective for the prophylaxis and treatment of these diseases.

Alginates are the main components of cell wall of brown algae, which are linear anion polysaccharides composed of β-D-mannuronic acid (ManA) and α-L-guluronic acid (GulA), linked by 1-4 glucosidic bonds. Alginate belongs to high polymers with a molecular weight of several $10^4$ to $10^6$ with abundant sources. Alginate has been widely applied in food production, chemical engineering and medicine, etc. Recent study has revealed that alginate has a variety of bioactivities. However, its application as a drug is limited to a certain extent by its large molecular weight. Therefore, the oligosaccharide degraded from alginate by different methods is highly valuable for glycochemistry, glycobiology, glycoengineering and study of saccharide-based drugs, etc. The methods for degrading alginate include enzymatic, physical and chemical degradation, yet the requirement of specific enzymes has limited the application of enzymatic degradation. Physical degradation, which is usually used in combination with other methods, cannot easily provide oligosaccharides due to the ultimate molecular weight of about 50,000 Da of the products thereof. Chemical degradation used for polysaccharides include acidic hydrolysis and oxidative degradation. Acidic hydrolysis is limited by its capacity to get oligosaccharides with a molecular weight of 4000 or less when conducted at a normal temperature and under a normal pressure.

DISCLOSURE OF INVENTION

To solve the above-describe problems and through deep studies of the inventors, it is found that an alginate oligosaccharide with a molecular weight of 4,000 or less can be obtained by acid hydrolysis at a high temperature and under a high pressure, and its derivatives whose reduced terminal in position 1 is carboxyl radical can be prepared in the presence of oxidants. The invention is completed on the above basis.

The present invention provides an alginate oligosaccharide and its derivatives with a low molecular weight, or pharmaceutically-acceptable salts thereof, and provides a process for preparing the same. The present invention also provides a medicament for the prophylaxis and treatment of AD and diabetes comprising the above-mentioned low molecular alginate oligosaccharide or its derivatives, or pharmaceutically-acceptable salts thereof.

The present invention relates to an alginate oligosaccharide represented by formula (I) and its derivatives or pharmaceutically-acceptable salts thereof. The said oligosaccharide is composed of β-D-mannuronic acids linked by α-1,4 glycosidic bonds,

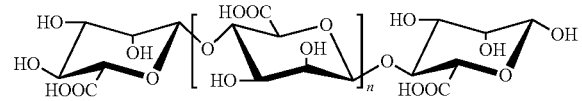

(I)

wherein, n represents 0 or an integer of 1 to 19.

In the present invention, an example of the said alginate oligosaccharide derivatives is a compound represented by formula (II), in which the reduced terminal in position 1 is carboxyl radical,

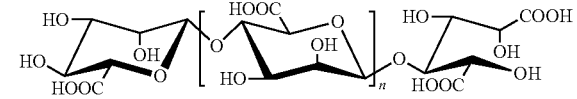

(II)

wherein, n represents 0 or an integer of 1 to 19.

In said formula (I) and (II), n is preferably 2 to 10, and more preferably 4 to 8. The reason that biological effects of tetrasaccharide to dodecasaccharide (preferably, hexasaccharide to decasaccharide) are better remains unclear, which may be caused by the liability of these oligosaccharides to be recognized and accepted by cells.

The said alginate oligosaccharide derivatives further include, for example, the derivatives, of which a part of the hydroxyl groups in mannuronic acid are sulfated.

The pharmaceutically-acceptable salts of the said alginate oligosaccharide and its derivatives can be, for example, salts of sodium, potassium, calcium, magnesium and the like. The sodium salts are preferred. The pharmaceutically-acceptable salts can be prepared by conventional methods.

The present invention also relates to a process for preparing the said alginate oligosaccharide and its derivatives, wherein an alginate solution is reacted for about 2 to 6 hrs in an autoclave at pH 2-6 and a temperature of about 100-120° C.; and its pH is then adjusted to about 7. The oxidative degradation product is obtained by the addition of an oxidant to the alginate oligosaccharide solution.

In a preferred embodiment of the invention, 0.5~5% sodium alginate aqueous solution is heated for 4 hrs in an autoclave at pH 4 and a temperature of 110° C. After the reaction is completed, the reactant is sucked out and cooled, and then the pH is adjusted to 7 by adding NaOH solution. While stirring, the filtrate is slowly poured into industrial alcohol which is 4 times as the volume of the filtrate, and stayed overnight to allow precipitation. The precipitate is filtered off with suction to dryness, and is dehydrated by washing with absolute ethanol. A white filter cake is obtained and dried in an oven at 60° C. to give a crude alginate oligosaccharide. The crude alginate oligosaccharide is formulated to a 10% solution, and is precipitated with 95% ethanol solution. The precipitate is washed with absolute ethanol, dried and formulated to a 5% solution. The solution is filtered through a 3 μm film to remove impurities, then desalted on a Bio-Gel-P6 column (1.6×180 cm) with 0.2 mol/L $NH_4HCO_3$ as the mobile phase and the product is collected by multiple steps. The elute is measured by the sulfate-carbazole method. The fractions containing saccharides are collected, concentrated under a reduced pressure and desalted, and lyophilized to give alginate oligosaccharides.

The preparation of the derivatives represented by formula (II) is as follows: an oxidant is added and reacted for 15 min to 2 hrs at the temperature of 100~120° C. after the above alginate solution is reacted for about 2 to 6 hrs in an autoclave at pH 2~6 and a temperature of about 100~120° C. In an embodiment of the invention, 25 ml of 5% copper sulfate solution is added to 50 ml of 10% NaOH (aq), mixed immediately, and immediately added with 40 ml of 5% alginate oligosaccharide solution. The resultant mixture is heated in a boiling water bath until no more brick red precipitate is generated. The mixture is centrifuged to remove the precipitates. Some supernatant is taken out and added to 10% NaOH (aq) and 5% copper sulfate solution according to the above ratio to check any generation of brick red precipitates. If negative, the supernatant is added to industrial alcohol which is 4 times the volume of the supernatant, and stayed overnight to allow precipitation. The precipitate is filtered off with suction to dryness, dehydrated with absolute ethanol repeatedly and dried in an oven at 60° C. Separation is carried out in the same way as of the alginate oligosaccharide of formula (I).

The invention also provides a pharmaceutical composition containing an effective amount of the said alginate oligosaccharide or its derivatives, or pharmaceutically-acceptable salts thereof and pharmaceutically-acceptable carriers.

The pharmaceutical composition can be used as a medicament for the prophylaxis and treatment of Alzheimer's disease.

Further, the pharmaceutical composition can be used as an amyloid-β protein fibrils forming inhibitor and fibrils disaggregating promoter.

The pharmaceutical composition can also be used as a medicament for the prophylaxis and treatment of diabetes.

Furthermore, the pharmaceutical composition can be used as pancreatic islet amyloid protein fibrils forming inhibitor and islet amyloid polypeptide inhibitor. In view of the current difficulty of lacking effective medicines for the prophylaxis and treatment of AD and diabetes, it is especially important that the alginate oligosaccharide of the present invention is used in the manufacture of a medicament for the prophylaxis and treatment of AD and diabetes.

EMBODIMENTS

1 Preparation of the Alginate Oligosaccharide 1 g sodium polymannanuronate (weight average molecular weight of 8,235 Da, provided by Lantai Pharm. LTD., Ocean University of China) is added to distilled water to obtain a 1% solution, adjusted pH to 4 with HCl, placed in an autoclave and heated at 110° C. for 4 h. After cooling, the solution pH is adjusted to 7 with NaOH (aq.). With stirring, the filtrate is slowly poured into industrial alcohol which is 4 times the volume of the filtrate, and stayed overnight to precipitate. The alcohol precipitate is filtered off with suction to dryness, and is dehydrated by washing with absolute ethanol. A white filter cake is obtained and dried in an oven at 60° C. to give a crude alginate oligosaccharide.

Figure 1:
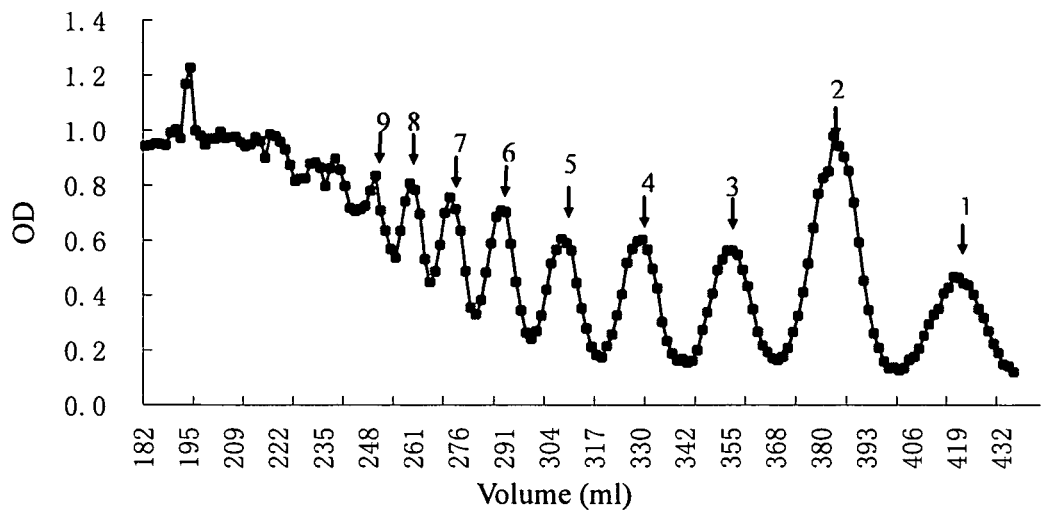
FIG. 1 is the eluting curve of the alginate oligosaccharide according to the present invention separated by a Bio-Gel-P6 column after acid hydrolysis.

The crude alginate oligosaccharide is formulated to a 10% solution, and is precipitated with 95% ethanol solution. The precipitate is washed with absolute ethanol, and formulated to a 5% solution after drying. The solution is filtered through a 3 μm film to remove impurities, and then desalted on a Bio-Gel-P6 column (1.6×180 cm) with 0.2 mol/L NH$_4$HCO$_3$ as the mobile phase and collected by multiply steps. The elute is measured by the sulfate-carbazole method, and the components including sugars are collected, concentrated under a reduced pressure and desalted on a G-10 column. The outer volume component is further separated by a Bio-Gel-P10 column (1.6×180 cm) and lyophilized to give a series of alginate oligosaccharides (FIG. 1).

2 Preparation of the Oxidative Degradation Product of the Alginate Oligosaccharide 5 g of the above-prepared alginate oligosaccharide is formulated to a 5% solution. 25 ml of 5% copper sulfate solution is added to 50 ml of 10% NaOH (aq), and mixed immediately, and immediately added with 40 ml of 5% alginate oligosaccharide solution. The resultant mixture is heated in a boiling water bath until no more brick red precipitate is generated. The mixture is centrifuged to remove precipitates. Some supernatant is taken out and added into 10% NaOH (aq) and 5% copper sulfate solution according to the above ratio to check for brick red precipitate. If negative, the supernatant is added to industrial alcohol which is 4 times the volume of the supernatant, and stayed overnight to allow precipitation. The precipitate is filtered off with suction to dryness, dehydrated with absolute ethanol repeatedly and dried in an oven at 60° C. Thus a crude oxidative product of alginate oligosaccharide is obtained.

Figure 2:
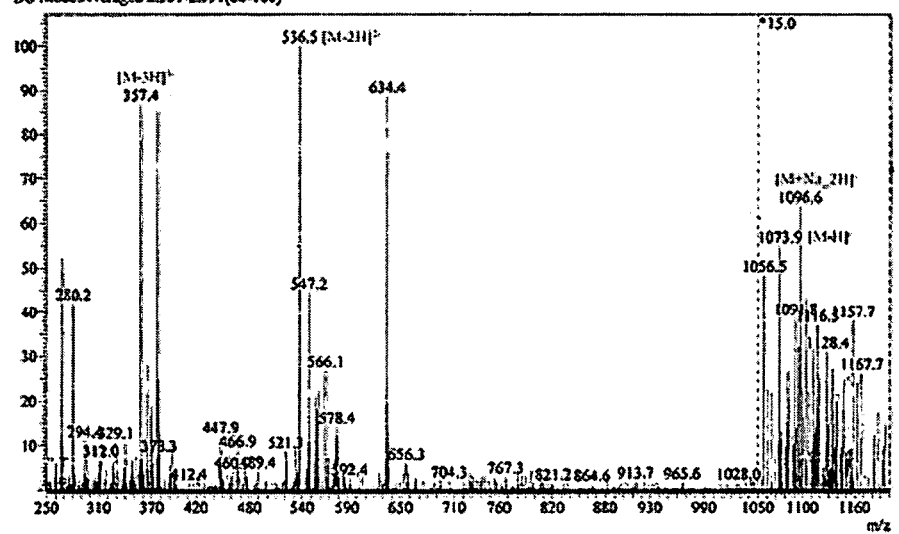
FIG. 2 is the MALDI-TOF spectrum of the alginate oligosaccharide according to the present invention.
Figure 3:
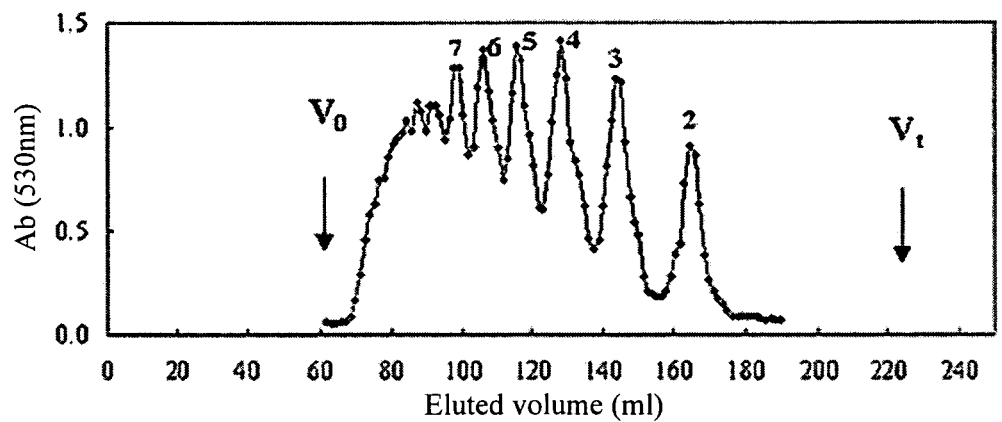
FIG. 3 is the eluting curve of the oxidative degradation product of the alginate oligosaccharide separated by a Bio-Gel-P6 column.

The crude oxidative degradation product of alginate oligosaccharide is formulated to a 10% solution, and precipitated with 95% ethanol solution. The precipitate is washed with absolute ethanol, and formulated to a 5% solution after drying. The solution is filter through a 3 μm film to remove the impurities, and then desalted on a Bio-Gel-P6 column (1.6× 180 cm) with 0.2 mol/L NH$_4$HCO$_3$ as the mobile phase and collected by multiple steps. The elute is measured by the sulfate-carbazole method, and the components including sugars are collected, concentrated under a reduced pressure and desalted on a G-10 column. The outer volume component is further separated by a Bio-Gel-P10 column (1.6×180 cm) and lyophilized to give a series of oxidative degradation products (FIG. 2).

3 Structure Identification of the Alginate Oligosaccharides

The structures of oligosaccharides contained in the fraction obtained from the preparation of the alginate oligosaccharides are identified. It is confirmed that the of oligosaccharides are alginate oligosaccharides composed of β-D-mannuronic acid linked by 1,4 glycosidic bonds. The structural formula is:

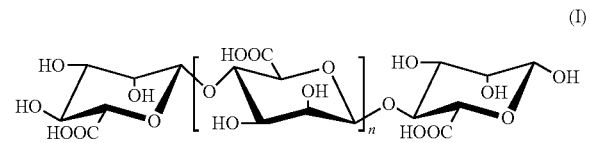

(I)

wherein, n represents 0 or an integer of 1 to 19.

Hereinafter, the fraction at about 292 ml of the elute (the fraction labeled as "6" in FIG. 1, hereinafter referred to as Component 6) is taken as an example to illustrate the structure analysis of above oligosaccharides.

3.1 Ultraviolet Absorption Spectrogram

The oligosaccharide fraction at about 292 ml of the elute is diluted to an appropriate concentration, and scanned at 190-400 nm with UV-2102 UV-VIS spectrophotometer. It is found that no specific absorption peak appears in the ultraviolet region, indicating that the structure is void of conjugated double bonds. However, non-specific absorption peak appears at 190~200 nm. Thus, during desalting the oligosaccharide, it can be on-line detected in above ultraviolet region.

3.2 Infrared Spectrum Analysis 0.5 mg of above oligosaccharide fraction is weighed. Infrared spectrum is determined with NEXUS-470 intelligent infrared spectrometer with KBr pellets. The peaks at 3420.79 cm$^{-1}$, 3214.64 cm$^{-1}$, and 2924.61 cm$^{-1}$ are attributable to symmetry stretching vibrations of hydroxyl group; the peak at 1600.25 cm$^{-1}$ is attributable to symmetry stretching vibration of carbonyl group of carboxylate; the peak at 1406.54 cm$^{-1}$ is attributable to shearing vibration of hydroxyl group; the peak at 1146.42 cm$^{-1}$ is attributable to symmetry stretching vibration of C—O bond of carboxyl group; the peak at 1045.77 cm$^{-1}$ is attributable to anti-symmetry stretching vibrations of anhydro ether; and the peak at 804.02 cm$^{-1}$ is attributable to anti-symmetry stretching vibrations of mannuronic acid cyclic skeleton. It is indicated that such compound has carboxyl group, hydroxyl group and mannuronic acid cyclic skeleton.

3.3 MS Analysis

MS analysis is performed with BIFLEX II type MALDI-TOF mass spectrometer (Bruker Daltonics Co.). As seen from the spectrum (FIG. 2, table 1), the peak of m/z 1073.9 is the molecular ion peak [M-H]$^{-1}$; the peak of m/z 1096.6 is [M+Na-2H]$^{-1}$; the peak of m/z 1028.0 is [M-H$_2$O—CO—H]$^{-1}$; the peak of m/z 821.2 is [M-ManA-CH$_2$O-2H2O—H]$^{-1}$; m/z 704.3 is [M-2ManA-H$_2$O—H]$^{-1}$; m/z 634.4 is [M-2ManA-2(CH$_2$O)—CO—H]$^{-1}$; the peak of m/z 536.5 is [M-2H]$^{2-}$; and the peak of m/z 357.4 is [M-3H]$^{3-}$. In ESI-MS spectrum of above oligosaccharide fraction, the molecular ion peak is m/z 1073.9, indicating that its molecular weight is 1074.

TABLE 1

| MS analysis of the alginate oligosaccharide (Component 6) | |
|---|---|
| Fragment ions | m/z |
| [M-H]$^{-1}$ | 1073.9 |
| [M + Na—2H]$^{-1}$ | 1096.6 |
| [M-H$_2$O—CO—H]$^{-1}$ | 1028.0 |
| [M-ManA-CH$_2$O—2H$_2$O—H]$^{-1}$ | 821.1 |
| [M-2ManA-H$_2$O—H]$^{-1}$ | 704.3 |
| [M-2ManA-2(CH$_2$O)—CO—H]$^{-1}$ | 634.4 |
| [M-2H]$^{2-}$ | 536.5 |
| [M-3H]$^{3-}$ | 357.4 |

3.4 Nuclear Magnetic Resonance Spectroscopy of the Alginate Oligosaccharide $^1$H NMR and $^{13}$C NMR of the alginate oligosaccharide represented by formula (I) (n=4) are obtained by JNM-ECP600 NMR spectrometer. The results are shown in table 2 and 3.

TABLE 2

| $^1$H-NMR analysis of the alginate oligosaccharide (Component 6) | | | | | |
|---|---|---|---|---|---|
| | Chemical shift (ppm) | | | | |
| | H-1 | H-2 | H-3 | H-4 | H-5 |
| r α | 5.21 | 3.98 | 4.03 | 4.04 | 4.16 |
| r β | 4.91 | 3.99 | 3.77 | 3.90 | 3.77 |
| m α | 4.69 | 4.03 | 3.75 | 3.93 | 3.69 |

TABLE 2-continued

<sup>1</sup>H-NMR analysis of the alginate oligosaccharide (Component 6)

| | Chemical shift (ppm) | | | | |
|---|---|---|---|---|---|
| | H-1 | H-2 | H-3 | H-4 | H-5 |
| m β | 4.64 | 4.03 | 3.75 | 3.65 | 3.69 |
| n | 4.63 | 3.74 | 3.63 | 3.75 | 4.01 |

TABLE 3

<sup>13</sup>C-NMR analysis of the alginate oligosaccharide (Component 6)

| | Chemical shift (ppm) | | | | | |
|---|---|---|---|---|---|---|
| | C-1 | C-2 | C-3 | C-4 | C-5 | C-6 |
| r α | 93.54 | 70.06 | 69.02 | 78.37 | 72.60 | 175.84 |
| r β | 93.74 | 70.42 | 71.60 | 78.28 | 76.08 | 175.84 |
| m | 99.08 | 70.63 | 71.43 | 78.07 | 75.90 | 175.41 |
| n | 100.15 | 68.48 | 72.47 | 76.27 | 70.05 | 175.27 |

According to above analysis results, it is confirmed that the alginate oligosaccharide in above fraction is mannuronic hexasaccharide having the following structure (Ia):

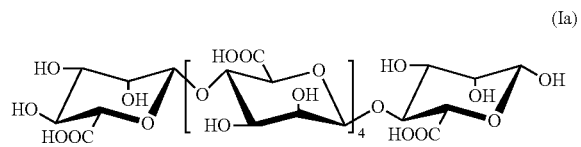

(Ia)

3.5 Determination of the Content of Mannuronic Acid in the Alginate Oligosaccharide (<sup>1</sup>H-NMR Spectroscopy)

The composition of the alginate oligosaccharide is determined by high-resolution <sup>1</sup>H-NMR to quantify the ratio of mannuronic acid to guluronic acid (M/G) in the alginate oligosaccharide according to the signal intensity of proton of anomeric carbon. 3 to 5 mg of dried sample is weighed, dissolved in $D_2O$ at neutral pD and added with 0.3 mg of EDTA. The sample is determined by Bruker DPX-300 NMR spectrometer. The spectrum is reported at 70° C., so that the peak of $D_2O$ is far away from the anomeric proton resonance region. The signal relative intensity is expressed by the integral of the peak area. The results indicate that H-1 signals of M radical appear at 4.64 ppm and 4.66 ppm (i.e. H-1 signals of M radical in MM and MG sequences, respectively); all of H-1 signals of G radical appear at 5.05 ppm (double peak). The relative content of M and G in the sample can be expressed by their H-1 peak intensity, as the following equation:

$$M\% = \frac{I_{4.64} + I_{4.66}}{I_{4.64} + I_{4.66} + I_{5.05}} \times 100\%$$

wherein, I represents the peak intensity, expressed by the integral of the peak area.

The relative content of D-mannuronic acid in the sample is 98.07% by the above method, indicating that the alginate oligosaccharide is mainly composed of mannuronic acid.

4 Structure Identification of the Oxidative Degradation Product of the Alginate Oligosaccharide The structure of the oligosaccharide oxidative degradation product in the fraction obtained from the preparation of the oxidative degradation product of the alginate oligosaccharide is identified. It is confirmed the oxidative degradation product is a derivative of the alginate oligosaccharide composed of β-D-mannuronic acid linked by 1,4-glycosidic bonds, in which the reduced terminal in position 1 is a carboxyl radical. The structural formula is:

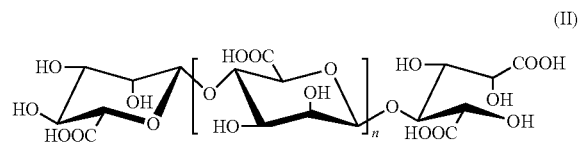

(II)

wherein, n represents 0 or an integer of 1 to 19.

Component 6 is taken as an example to illustrate the structure analysis of the above oligosaccharide oxidative degradation product.

4.1 Ultraviolet Absorption Spectrogram

An appropriate amount of oxidative degradation product is diluted to a certain concentration with distilled water, and scanned with Shimdzu UV-260 UV spectrophotometer (190 nm~700 nm) at full wavelength. It is found that no specific absorption peak appears in ultraviolet and visible light regions.

4.2 Infrared Spectrum Analysis

Infrared spectrum of the oxidative degradation product of the alginate oligosaccharide is determined by NICOLE NEXUS-470 intelligent infrared spectrometer. The results are shown in table 4.

TABLE 4

IR spectrum of the oxidative degradation product of the alginate oligosaccharide

| Absorption peak (cm<sup>-1</sup>) | Type of vibration | Group | Intensity |
|---|---|---|---|
| 3400.56 | $v_{OH}$ | —OH | s |
| 3219.02 | $v_{OH}$ | —OH | s |
| | $v_{CH}$ | —COOH | |
| 2924.65 | $v_{OH}$ | —COOH | m |
| 1599.76 | $v_{C=O}$ | —COOH | s |
| 1405.95 | $v_{C—O}$ | —COOH | s |
| 1296.26 | $\delta_{O—H}$ | —OH | m |
| 1037.84 | $v_{as}$(C—O—C) | anhydro ether | m |
| 817.14 | $v_{as}$ (sugar ring) | mannuronic acid cyclic skeleton | m |
| 669.80 | $\gamma_{OH}$ | —OH | m |

4.3 <sup>1</sup>H-NMR Analysis

<sup>1</sup>H-NMR and <sup>13</sup>C-NMR spectrums of the oxidative degradation product are obtained by Bruker Auance DPX-300 NMR spectrometer. As seen from <sup>1</sup>H-NMR spectrum, it is mainly composed of the signals of six hydrogen atoms in β-D-mannuronic acid. After coupling pattern of each signal is assigned, it is found that the oxidative degradation product of the alginate oligosaccharide is mainly composed of mannuronic acid. If the reduced terminal in position 1 is aldehyde group, chemical shifts of H-1α and H-1β should be 5.11 ppm and 4.81 ppm, respectively. Since the reduced terminal in position 1 of the alginate oligosaccharide is oxidated to carboxyl group from aldehyde group, H-1 disappears, thus signals at 5.11 ppm and 4.81 ppm disappear. As seen from <sup>13</sup>C-NMR spectrum, it is mainly composed of the signals of six carbon atoms in β-D-mannuronic acid. After coupling pattern of each signal is assigned, it is found that the intermediate molecule is mainly composed of mannuronic acid.

Compared with the spectrum of the intermediate, the signal of the reduced terminal C-1 of mannuronic acid (94 ppm) disappears. The signal of the reduced terminal C-1 (175.81 ppm) is shifted towards low field. The reason is that the reduced terminal in position 1 of the alginate oligosaccharide is oxidated to carboxyl group from aldehyde group and the chemical shift of C-1 is changed from about 94 ppm of aldehyde group to 175.81 ppm of carboxyl group.

4.4 MS Analysis

Figure 4:
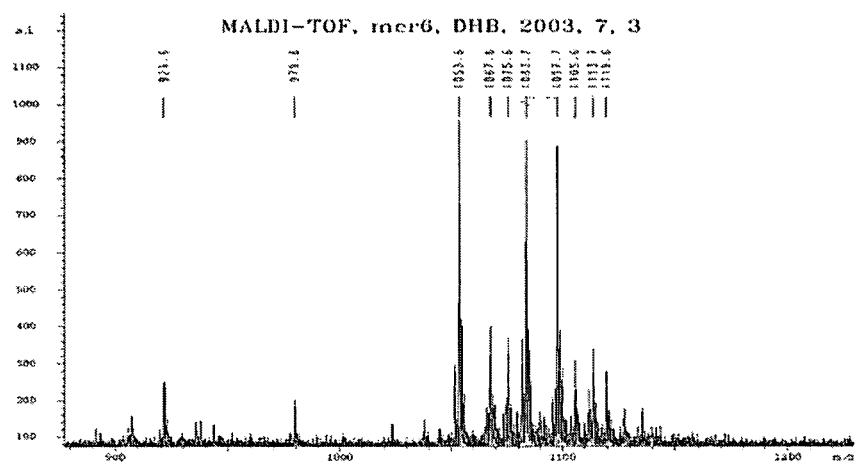
FIG. 4 is the MALDI-TOF spectrum of the oxidative degradation product of the alginate oligosaccharide (Posotive mode).

MS analysis is performed with BIFLEX III type MALDI-TOF mass spectrometer (Bruker Daltonics Co.). The results are shown in FIG. 4. As seen from FIG. 4, the peak of m/z 1113.7 is $[M+Na]^{+1}$; the peak of m/z 1113.7 is $[M-O+Na]^{+1}$; the peak of m/z 1083.7 is $[M-CH_2O+Na]^{+1}$; the peak of m/z 1067.6 is $[M-CH_2O-O+Na]^{+1}$; the peak of m/z 1053.6 is $[M-2(CH_2O)+Na]^{+1}$; the peak of m/z 979.6 is $[M-3(CH_2O)-CO_2+Na]^{+1}$; and the peak of m/z 921.6 is $[M-4(CH_2O)-CO_2-CO+Na]^{+1}$. MS analysis of the oxidative degradation product of the alginate oligosaccharide is shown in table 5.

TABLE 5

MS analysis of the oxidative degradation product of the alginate oligosaccharide

| Fragment ions | m/z |
| --- | --- |
| $[M + Na]^{+1}$ | 1113.7 |
| $[M-O + Na]^{+1}$ | 1097.7 |
| $[M-CH_2O + Na]^{+1}$ | 1083.7 |
| $[M-O\text{—}CH_2O + Na]^{+1}$ | 1067.6 |
| $[M-2(CH_2O) + Na]^{+1}$ | 1053.6 |
| $[M-3(CH_2O)-CO_2 + Na]^{+1}$ | 979.6 |
| $[M-4(CH_2O)-CO_2-CO + Na]^{+1}$ | 921.6 |

In MALDI-TOF spectrum of the oxidative degradation product of the alginate oligosaccharide, the peak of m/z 1113.7 is $[M+Na]^{+1}$, indicating that molecular weight of the oxidative degradation product the alginate oligosaccharide is 1090.7. The molecular weight increased sixteen compared with that of acid hydrolyzed alginate oligosaccharide (M=1075), that is, an oxygen atom is added into the molecule, which can be considered that the alginate oligosaccharide is oxidated during the preparation.

According to above analysis results, the structure of the oxidative degradation product of the alginate oligosaccharide is the formula (IIa):

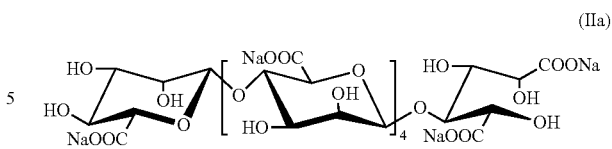

(IIa)

5 Evaluation of the Alginate Oligosaccharide on Alzheimer's Disease (AD)

A 6-mer separated with Bio-Gel-P6 column is used as an example to show its activity. So the alginate oligosaccharide is referred as "6-mer" in the following experiments.

5.1 Effects of 6-mer on AD Mice Induced by $A\beta_{1-40}$

Male Balb/c mice (18-22 g, purchased from Laboratory Centre of Shandong University) are weighed and randomly assigned to six groups as follows: a control group, a model group, a low-concentration (15 mg/kg) 6-mer-treated group, a middle-concentration (30 mg/kg) 6-mer-treated group, a high-concentration (60 mg/kg) 6-mer-treated group, and a Huperzine A-treated (HBY, with a concentration of 0.2 mg/kg) group. The mice were oral administered with corresponding drugs on day 3 after grouping. The drugs were administered once a day consecutively with a dosage of 0.5 ml/20 g until the experiment is completed. The mice of control and model groups were simultaneously administered with an equivalent amount of normal saline.

Figure 6:
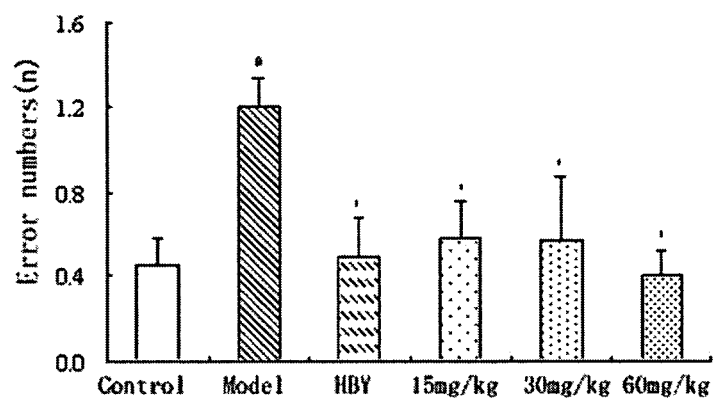
FIG. 6 shows the effect of the alginate oligosaccharide according to the present invention on the error numbers of AD mice induced by $A\beta_{1-40}$.

On the $8^{th}$ day after drug administration, mice are injected with aged $A\beta_{1-40}$ except the vehicle group as the method of reference (Jhoo J H et al., β-amyloid (1-42)-induced learning and memory deficits in mice: involvement of oxidative burdens in the hippocampus and cerebral cortex. *Behavioural Brain Research* (2004) 155: 185-196) to induce the AD model. Aged $A\beta_{1-40}$ solution is injected into the right cerebral ventricle. The results of acquisition trials tested with Morris water maze show that Aβ-treated mice display a longer escape latency (P<0.05, P<0.01), compared with the control and model groups, indicating that the AD model mice are established (FIG. 6). However, on the 1st day of test, this increased escape latency is shortened in all drug-treated groups except the group treated with 15 mg/kg of 6-mer. And the escape latency of 60 mg/kg 6-mer-treated group has statistical significance compared with that of the model group (P<0.05). On the 2nd and 3rd day of test, the escape latency of all drug-treated groups are shortened, wherein that of 60 mg/kg 6-mer-treated group and HBY-treated group have statistical significance compared with that of the model group (P<0.05).

TABLE 6

Effects of 6-mer on escape latency of AD mice induced by $A\beta_{1-40}$ tested with Morris water maze ($\bar{x} \pm SE$)

| Group | Dose (mg/kg) | n | Escape latency (s) | | |
| --- | --- | --- | --- | --- | --- |
| | | | 1st day | 2nd day | 3rd day |
| Control | — | 12 | 49.40 ± 8.39 | 54.30 ± 11.39 | 42.80 ± 10.04 |
| Model | — | 14 | 87.20 ± 7.58[##] | 93.46 ± 8.67[#] | 97.31 ± 8.65[##] |
| 6-Mer | 15 | 14 | 90.07 ± 10.71 | 83.29 ± 9.53 | 72.83 ± 12.50 |
| | 30 | 14 | 77.71 ± 8.69 | 71.69 ± 10.11 | 68.45 ± 14.46 |
| | 60 | 13 | 56.92 ± 9.92* | 63.57 ± 10.54* | 62.50 ± 13.10* |
| HBY | 0.2 | 14 | 76.29 ± 9.74 | 64.58 ± 10.36* | 63.83 ± 10.12* |

[#]p < 0.05,
[##]p < 0.01 vs control;
*p < 0.05 vs model

On the 4th day of Morris water maze test, the original plate is removed and the percentage of time of mice staying at the phase of original plate within 60 s is recorded. The results show that mice in the model group exhibit much lower latency bias than the control group (P<0.05), and the latency bias is elevated significantly after the administration of 6-mer compared with that of the model group (P<0.05) (table 7).

TABLE 7

Effects of 6-mer on the probe trial of AD mice induced by $A\beta_{1-40}$ tested with Morris water maze ($\bar{x} \pm SE$)

| Group | Dose (mg/kg) | n | Latency bias(%) |
|---|---|---|---|
| Control | — | 12 | 29.48 ± 5.47 |
| Model | — | 14 | 11.83 ± 3.33# |
| 6-Mer | 15 | 14 | 19.67 ± 5.15 |
|  | 30 | 14 | 22.99 ± 5.79 |
|  | 60 | 13 | 28.44 ± 6.08* |
| HBY | 0.2 | 14 | 22.18 ± 5.93 |

$P < 0.05$ vs control;
*$P < 0.05$ vs model

On the 25th day after Aβ injection, mice are further trained for step-through passive avoidance task. In the task, each mouse is placed in the illuminated compartment of the apparatus, facing away from the dark compartment, and the door is opened, allowing access to the dark compartment. Once the mouse enters the dark compartment, it receives an inescapable electric shock on the feet (36 V) through the stainless steel grid floor. The test is similarly performed after 24 h. The entry time of each mouse into the dark chamber (step-through latency, maximum testing limited to 3 min) and the number of entries into the dark compartment (number of errors) are recorded.

Figure 5:
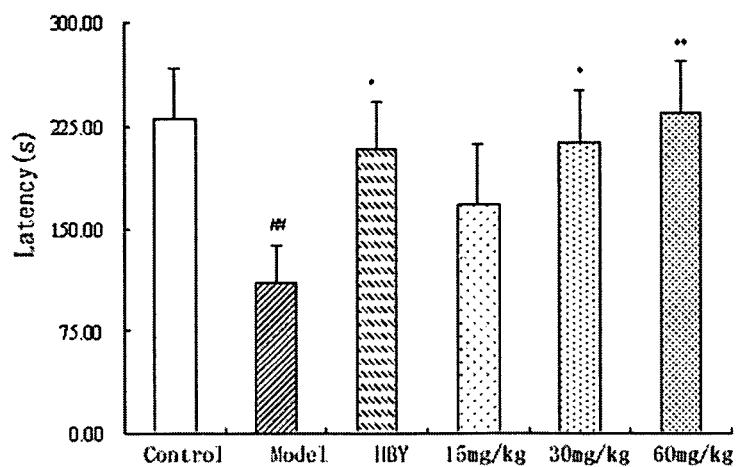
FIG. 5 shows the effect of the alginate oligosaccharide according to the present invention on the latency of AD mice induced by $A\beta_{1-40}$.

The results of step-through passive avoidance task are shown in FIGS. 5 and 6. Each group has 8 animals. The data are presented as mean±SE. The symbol # means significant difference compared with the control group (P<0.05). * means significant difference compared with the model group (P<0.05). The step-through latency of $A\beta_{1-40}$-treated group is shortened (P<0.01) and the error number is increased (P<0.05) compared with that of the control group, indicating the successful establishment of AD mice. However, the step-through latency is significantly prolonged in 30 and 60 mg/kg 6-mer-treated groups and HBY-treated group, and the number of errors is significantly reduced in 6-mer and HBY-treated groups, indicating that 6-mer has the function of significantly improving learning and memory activity in $A\beta_{1-40}$-induced models.

Effects of 6-mer on the Brain Biochemical Indicators of Aβ-Induced AD Mice

Following the behavioral test, rats are decapitated. Cerebral cortex and hippocampus are dissected on ice immediately, and stored at −80° C. after quick freezing in liquid nitrogen for 1 hour. MDA, SOD, GSH-PX, $Na^+$, $K^+$-ATPase, AchE and CHAT activities in the brain regions are determined using the respective kits. The homogenates of cerebral cortex and hippocampus are prepared with saline with a final concentration of 10% and 5%. The supernatant were obtained after centrifuging at 3600 rpm to test MDA, CuZn-SOD, GSH-PX, $Na^+K^+$-ATPase, AchE, and CHAT activities. The activity of ChAT is determined with isotope-labeled method. The other indexes and amount of total proteins are tested with the respective kits supplied by Nanjing Jiancheng Bioengineering Institute.

(1) Effects of 6-mer on the ChAT Activity of AD Mice

The ChAT activity in the cerebral cortex is markedly decreased after treatment with Aβ, as compared to the control group (p<0.05). However, its activity is increased after the treatment of 6-mer and HBY, wherein the curative effects of 30 mg/kg and 60 mg/kg of 6-mer and HBY have a statistically significance (table 8).

TABLE 8

Effects of 6-mer on the cerebral cortex ChAT activity of $A\beta_{1-40}$-induced AD mice (n = 10, $\bar{x} \pm SE$)

| Group | Dose (mg/kg) | ChAT activity (pmol/mg prot./min) |
|---|---|---|
| Control | — | 92.17 ± 2.95 |
| Model | — | 77.26 ± 4.9# |
| 6-Mer | 15 | 90.94 ± 3.77 |
|  | 30 | 99.98 ± 5.07** |
|  | 60 | 94.69 ± 5.83* |
| HBY | 0.2 | 100.70 ± 5.99** |

$P < 0.05$ vs control;
*$P < 0.05$,
**$P < 0.01$ vs model (2) Effects of 6-mer on the SOD Activity of AD Mice The SOD activity in brain is decreased after treatment with Aβ, but has no statistically significance as compared with the control group. Its activity is significantly increased both in cerebral cortex and hippocampus after the treatment of 6-mer at a dosage of 60 mg/kg, indicating that the mechanism of effect of 6-mer on AD is related to the improvement of the antioxidant activity (table 9).

TABLE 9

Effects of 6-mer on the SOD activity of the cerebral cortex and hippocampus of $A\beta_{1-40}$-induced AD mice (n = 10, $\bar{x} \pm SE$)

| Group | Dose (mg/kg) | SOD activity (NU/mg prot.) | |
|---|---|---|---|
|  |  | cerebral cortex | hippocampus |
| Control | — | 53.48 ± 1.56 | 66.35 ± 4.74 |
| Model | — | 49.99 ± 2.41 | 62.24 ± 4.16 |
| 6-Mer | 15 | 49.35 ± 2.27 | 69.76 ± 6.12 |
|  | 30 | 51.84 ± 2.07 | 61.72 ± 4.27 |
|  | 60 | 57.50 ± 2.51* | 79.97 ± 7.34* |
| HBY | 0.2 | 48.95 ± 2.13 | 69.91 ± 6.51 |

*$P < 0.05$ vs model (3) Effects of 6-mer on the MDA Content of AD Mice

The MDA content in the cerebral cortex and hippocampus has no significant difference as compared with the control group. Its content is decreased in brain after the treatment of HBY and 6-mer at a dosage of 30 mg/kg and 60 mg/kg, indicating that both of them have the ability to improve the response to oxidation and damage of free radicals in brain and protect the brain from oxidative damage (table 10).

TABLE 10

Effects of 6-mer on the MDA content of the cerebral cortex and hippocampus of $A\beta_{1-40}$-induced AD mice (n = 10, $\bar{x} \pm SE$)

| Group | Dose (mg/kg) | MDA content (nmol/ml) | |
|---|---|---|---|
|  |  | cerebral cortex | hippocampus |
| Control | — | 2.61 ± 10.22 | 4.75 ± 0.66 |
| Model | — | 2.18 ± 0.23 | 5.17 ± 0.47 |
| 6-mer | 15 | 1.79 ± 0.15 | 4.28 ± 0.82 |
|  | 30 | 1.87 ± 0.18 | 2.48 ± 0.43** |
|  | 60 | 1.47 ± 0.11** | 2.18 ± 0.43** |
| HBY | 0.2 | 1.61 ± 0.13* | 2.26 ± 0.39** |

*$P < 0.05$,
**$P < 0.01$ vs model (4) Effects of 6-mer on the GSH-PX Activity of AD Mice The GSH-PX activity in cerebral cortex and hippocampus is decreased after usage of Aβ with significant difference to the control group in hippocampus (p<0.05). Its activity is increased in cerebral cortex after the treatment of 6-mer, wherein the activity is significantly different after the treatment of the alginate oligosaccharide at a dosage of 60 mg/kg and HBY (p<0.05). The results are shown in table 11.

TABLE 11

Effects of 6-mer on the GSH-PX activity in the cerebral cortex and hippocampus of $A\beta_{1-40}$-induced AD mice (n = 10, $\bar{x} \pm SE$)

| | | GSH-PX (U/mg prot.) | |
|---|---|---|---|
| Group | Dose (mg/kg) | cerebral cortex | hippocampus |
| Control | — | 7.81 ± 1.20 | 5.39 ± 0.67 |
| Model | — | 6.43 ± 1.56 | 3.13 ± 0.58# |
| 6-Mer | 15 | 8.53 ± 0.86 | 4.13 ± 0.58 |
| | 30 | 7.12 ± 1.10 | 4.25 ± 0.54 |
| | 60 | 10.75 ± 1.80* | 4.81 ± 0.95 |
| HBY | 0.2 | 8.85 ± 1.33 | 5.29 ± 0.99* |

P < 0.05 vs control;
*P < 0.05 vs model (5) Effects of 6-mer on the $Na^+$, $K^+$-ATPase Activity of AD Mice The $Na^+$, $K^+$-ATPase activity in cerebral cortex and hippocampus is significantly decreased after treatment with Aβ as compared with the control group, indicating that Aβ significantly affected the energy metabolism of neurons in brain. However, its activity is markedly increased after the treatment of the alginate oligosaccharide at three different dosages, wherein the activity is significantly increased after the 60 mg/kg treatment in hippocampus as compared with HBY, indicating that improvement of the level of energy metabolism in brain may be one of the mechanisms of the alginate oligosaccharide to protect brain functions and anti-AD. The results are shown in table 12.

TABLE 12

Effects of 6-mer on the $Na^+$, $K^+$-ATPase activity in cerebral cortex and hippocampus of $A\beta_{1-40}$-induced AD mice (n = 10, $\bar{x} \pm SE$)

| | | ATPase activity (μmol Pi/mg prot./hour) | |
|---|---|---|---|
| Group | Dose (mg/kg) | cerebral cortex | hippocampus |
| Control | — | 1.06 ± 0.05 | 2.65 ± 0.38 |
| Model | — | 0.89 ± 0.06# | 1.62 ± 0.17# |
| 6-Mer | 15 | 1.08 ± 0.06* | 2.10 ± 0.29 |
| | 30 | 1.09 ± 0.08* | 2.07 ± 0.23 |
| | 60 | 1.08 ± 0.05* | 2.52 ± 0.25* |
| HBY | 0.2 | 0.91 ± 0.05 | 2.35 ± 10.43 |

P < 0.05 vs control;
*P < 0.05 vs model 5.2 Protective Effects of 6-Mer on Neurons Imp Aired by Aβ In Vitro The primary cerebral cortex neurons of rat are cultured as the method of reference (Banker G A, et al., Rat hippocampal neurons in dispersed cell culture. *Brain Res*, 1977, 126:397-425). The cells cultured for 1 week are used in this experiment. That is to say, on the $8^{th}$ day the cells are pretreated with a series of concentrations of 6-mer (final concentration of 0, 10, 50, 100 μg/ml) for 24 h, followed by the addition of aged $A\beta_{25-35}$ (Firstly resolved in distilled water with a concentration of 1 mg/ml, then stayed at 37° C. for 7 days to get aged $A\beta_{25-35}$ and stored at −20° C. for use) with a final concentration of 30 μM. After 24 h at 37° C., 10 μl of MTT with a concentration of 5 mg/ml is added. After 4 h at 37° C., the supernatant is removed and 150 μl of DMSO is added. Then the absorbance at 570 nm (630 nm as reference) is recorded with an ELISA reader (Rainbow, TECAN, Austria).

It is found that after the primary neurons are incubated with 30 μM of aged $A\beta_{25-35}$, the reduction of MTT is remarkably decreased and the survival rate of the cells is significantly reduced to 54.5±8.9% (P<0.001) after the treatment of aged $A\beta_{25-35}$. 6-mer at dosage of 10, 50, 100 μg/ml could significantly increase the survived cells impaired by $A\beta_{25-35}$ in a dose-dependent manner (the survived rate is 72.0±11.2%, 77.1±8.1% and 82.3±11.6% respectively).

Figure 7:
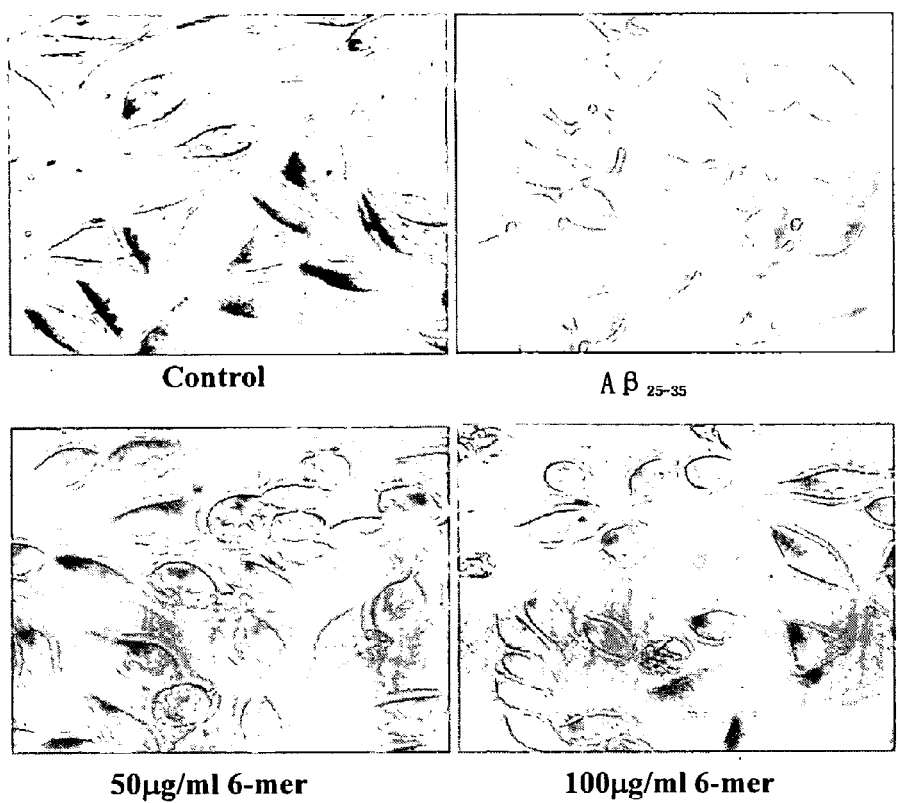
FIG. 7 shows the protective effects of the alginate oligosaccharide according to the present invention on SH-SY5Y cells impaired by $A\beta_{25-35}$.
Figure 8:
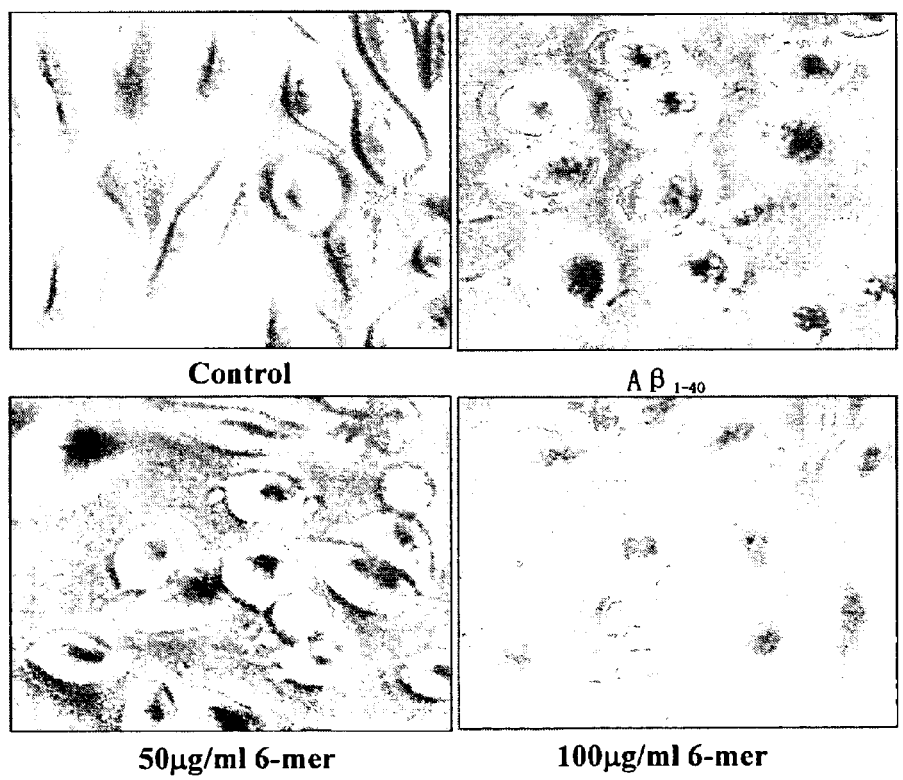
FIG. 8 shows the protective effects of the alginate oligosaccharide according to the present invention on SH-SY5Y cells impaired by $A\beta_{1-40}$.

6-mer has similar protective effects on neuron cell line SH-SY5Y as the primary neurons. SH-SY5Y impaired with 30 μM of aged $A\beta_{25-35}$ (FIG. 7) and 2 μM of $A\beta_{1-40}$ (FIG. 8) for 48 h could induce a series of changes, for example, damage to the cells, reduced number of cells, occurrence of some round cells and suspension cells. Further, the survival rate of the cells is reduced to 73.3±9.4% and 64.1±2.5% respectively. However, the alginate oligosaccharide at a dosage of 50 and 100 μg/ml could significantly inhibit the neurotoxicity of Aβ, for example, the occurrence of suspension cells is reduced and the survival rate is increased.

The above experiments revealed that 6-mer could shorten the escape latency and increase the numbers of crossing the original plate and shorten the time of arriving the original plate on AD mice induced with $A\beta_{1-40}$, implying its behavioural improvement activity in Aβ-treated mice. This in vivo result as well as the in vitro protective effects on primary and neuron cell lines suggests that 6-mer has the anti-AD activity.

6 Action Mechanism Study of 6-mer on AD 6.1 Effects of 6-mer on the Apoptosis of Cell Line SH-SY5Y Induced by $A\beta_{25-35}$ SH-SY5Y cells are incubated in 6-well plates at a density of $2 \times 10^5$ cells per well. The day after plating, cells are pretreated with varying concentrations (0, 50, 100 μg/ml) of 6-mer for 24 h, followed by the addition of 30 μM aged $A\beta_{25-35}$ (purchased from Sigma. Co.). After 48 h at 37° C., cells are digested, collected, washed, centrifuged at 1200 rpm and incubated with 200 ml of a mixture of 5 mg/ml propidium iodide (Hyclone Co.) and 100 U/ml RNase (Hyclone Co.). Then the cells are measured by flow cytometry (BD Co., US), with 8000 cells per sample It is found that SH-SY5Y cells stimulated with 30 μM aged $A\beta_{25-35}$ for 48 h show 24.8±1.9% hypodiploid cells. However, pretreatment with 50 and 100 μg/ml 6-mer for 24 h significantly suppressed apoptosis induced by aged $A\beta_{25-35}$, and the observed percentages of hypodiploid cells are 10.2±1.3% and 5.1±0.7%, respectively.

Furthermore, it is found that 6-mer also significantly arrests apoptotic cascade by reversing overload of intracellular calcium ion and ROS accumulation, and by up-regulating the expression of Bcl-2 and down-regulating the expression of P53 and Caspase-3 induced by Aβ. All these factors contribute to the therapeutic potential of 6-mer in the treatment of AD.

6.2 Molecular Mechanism of 6-mer on Anti-Neuron Toxicity of Aβ

(1) Effects of 6-mer on the Fibril Formation of $A\beta_{1-40}$

Fresh $A\beta_{1-40}$ is incubated alone or with 6-mer (final concentration of 10, 50, and 100 μg/ml, respectively) at 37° C. for 24 h. After incubation, Th-T is added and fluorescence intensity is monitored at Em=450 nm and Ex=480 nm.

Figure 9:
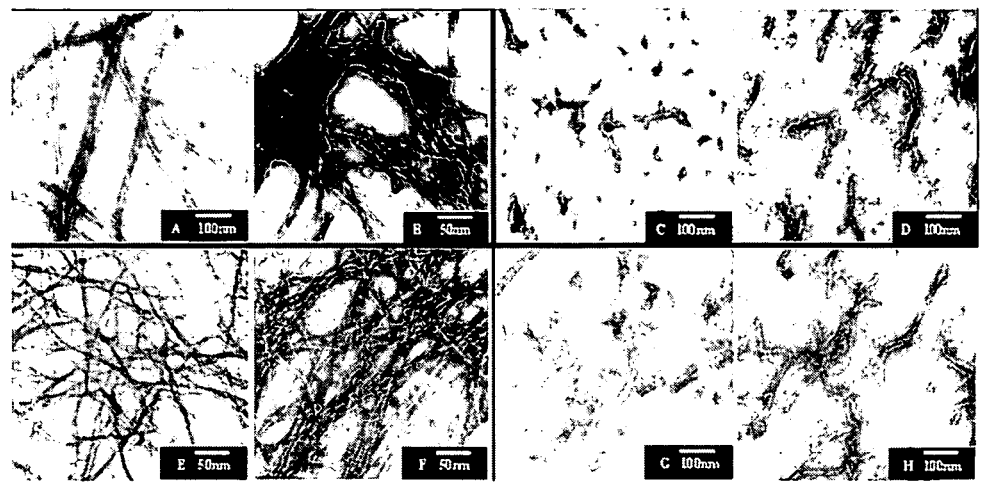
FIG. 9 shows the inhibitory effects of the alginate oligosaccharide according to the present invention on the normal and heparin-induced fibril formation of $A\beta_{1-40}$.

The results show that 6-mer (at a dosage of 10, 50, 100 μg/ml) can inhibit the accumulation of $A\beta_{1-40}$, wherein the inhibitory effect of 100 μg/ml 6-mer is most obvious. The fluorescence intensity is 10.46±0.94, 9.18±1.32 and 7.81±1.38 (p<0.05, 0.05 and 0.001, respectively), respectively. The same effects of 6-mer on the fibril formation of $A\beta_{1-40}$ are studied with TEM (FIG. 9), indicating that 6-mer can significantly inhibit the fibril formation of $A\beta_{1-40}$. Further, it is found that 6-mer show significant inhibitory effect on the fibril formation of $A\beta_{1-40}$ facilitated by heparin using TEM. In FIG. 9, A shows the result of incubation with $A\beta_{1-40}$ alone for 24 h; B shows the result of incubation with a mixture of $A\beta_{1-40}$ and heparin 24 h; C shows the result of incubation with a mixture of $A\beta_{1-40}$ and 6-mer for 24 h; D shows the result of incubation with a mixture of $A\beta_{1-40}$, heparin and 6-mer for 24 h; E shows the result of incubation with $A\beta_{1-40}$ alone for 48 h; F shows the result of incubation with a mixture of $A\beta_{1-40}$ and heparin for 48 h; G shows the result of incubation with a mixture of $A\beta_{1-40}$ and 6-mer for 48 h; and H shows the result of incubation with a mixture of $A\beta_{1-40}$, heparin and 6-mer for 48 h.

(2) Effects of 6-mer on the Destability of $A\beta_{1-40}$ Fibril.

Figure 10:
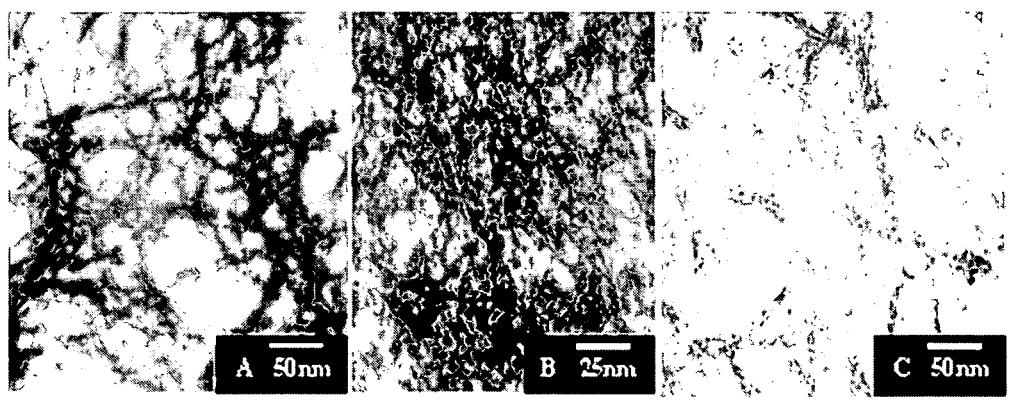
FIG. 10 shows the destability of the alginate oligosaccharide according to the present invention on fibril $A\beta_{1-40}$.

1 mg/ml of distilled water-resolved $A\beta_{1-40}$ is aged at 37° C. for 7d, after which it is exposed to 6-mer for 3 days. The sample is stained with uranium acetate and TEM (JEM 1200EX) reveals that $A\beta_{1-40}$ alone leads to the formation of long, twisted fibers after aging for 7 days (FIG. 10A). In the presence of heparin for an additional 24 h, the long, twisted fibers become much denser and longer compared to those formed in the absence of heparin (FIG. 10B). Notably, in the presence of 6-mer for an additional 3 days, the long and aggregated $A\beta$ fibers are turned into small irregular short fibers (FIG. 10C). These findings suggest that 6-mer is capable of reversing preformed $A\beta$ fibril, highlighting the destabilizing action of 6-mer on preformed $A\beta$ fibril and thus potentially therapeutic intervention.

(3) Effects of 6-mer on the Conformation of $A\beta_{1-40}$

Figure 11:
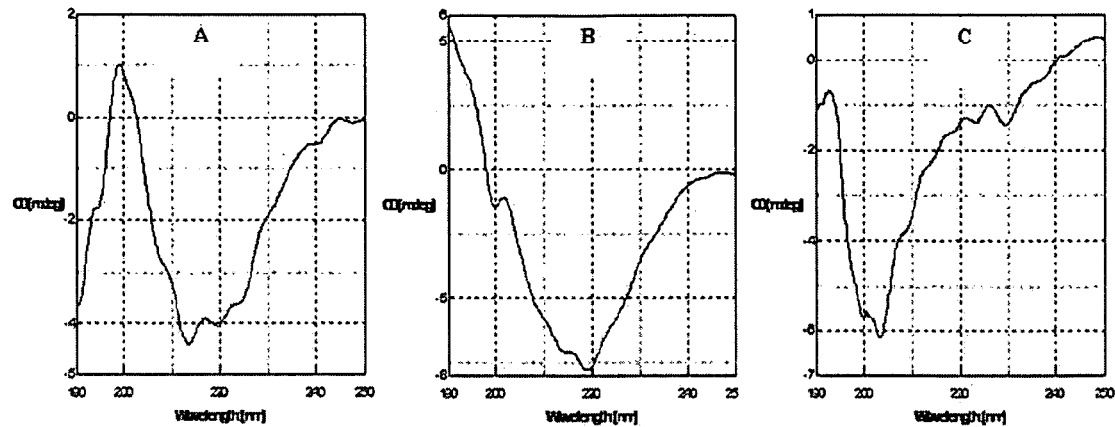
FIG. 11 shows the effects of the alginate oligosaccharide according to the present invention on the conformation of soluted 250 μg/ml $A\beta_{1-40}$.

CD spectra (J-500A, JASCO, Japan) of monomeric $A\beta_{1-40}$ (250 μg/ml in TBS (100 mM Tris, 50 mM NaCl, pH7.4)) incubated at 37° C. for 12 h is mainly characterized by β-sheet secondary structure (FIG. 11A). The simultaneous exposure of monomeric $A\beta_{1-40}$ to 6-mer (100 μg/ml) for 12 h prevents the β-sheet formation (FIG. 11C). However, heparin significantly accelerates the conformational transition to β-sheet structure (FIG. 11B).

(4) Interaction Between 6-mer and $A\beta$

SPR technique (BIAcore X, Uppsala, Sweden) is used to characterize the interaction of 6-mer and $A\beta$. Different degree of aged $A\beta_{1-40}$ (aged for 0, 0.5, 1, 2, 4, 6 d at 37° C.) in HBS EP buffer solution (0.01 MHEPES, 150 mmol/L NaCl, 3.4 mmol/L EDTA-$Na_2$, 0.005 vol % Tween-20, pH 7.4) with 5 concentrations are flowed through the 6-mer-immobilized sensor chip. The flow rate is 5 μl/min, and the injection volume is 10 μl. The binding sensorgramm is recorded and the sensor chip is regenerated with 2M NaCl.

It is found that different degrees of aged $A\beta_{1-40}$ all can bind to 6-mer. The binding affinity is weakest for fresh $A\beta_{1-40}$ and 6-mer with a $K_D$ value of 6.85E-07 M. The binding affinity increases with aged degree ($K_D$ values are 1.07E-07, 9.06E-08, 5.43E-08, 2.15E-08, 1.45E-08 M, respectively), and becomes essentially stable after aging for 2 days.

Further studies reveal that 6-mer binds to the full length $A\beta$ through His13~Lys16, and binds to $A\beta_{25-35}$ through Ser26~Lys28. The binding of 6-mer with fresh $A\beta$ might contributed to its inhibition on fibrillogenesis of $A\beta$. The binding of 6-mer with aged $A\beta$ might contributes to the destability of $A\beta$ fibril.

The above studies reveal that the molecular mechanisms are attributed to the fact that 6-mer both hinder the whole fibrillogenetic process and particularly disassemble the preformed $A\beta$ fibril. These results indicate that 6-mer, acting as a full $A\beta$ cascade antagonist, is a potential preventive and therapeutic candidate for AD, which provides the proof of the principle for a new strategy for the treatment of AD.

7 Study of 6-mer on Diabetes Models 7.1 Protective Effects of 6-mer on Pancreatic Beta-Cells Impaired by Amylin In Vitro The human pancreatic beta-cells cell line NIT is cultured with DMEM medium containing 10% FBS. The cells are incubateded into 96-well plates in density of $1 \times 10^4$ cells/well. The day after plating, they are pretreated with varying concentrations of 6-mer (final concentration of 0, 10, 50, 100 μg/ml) for 24 h, followed by the addition of aged amylin with a final concentration of 30 μM. After 48 h at 37° C., the survival of the cells is measured by MTT method.

Figure 12:
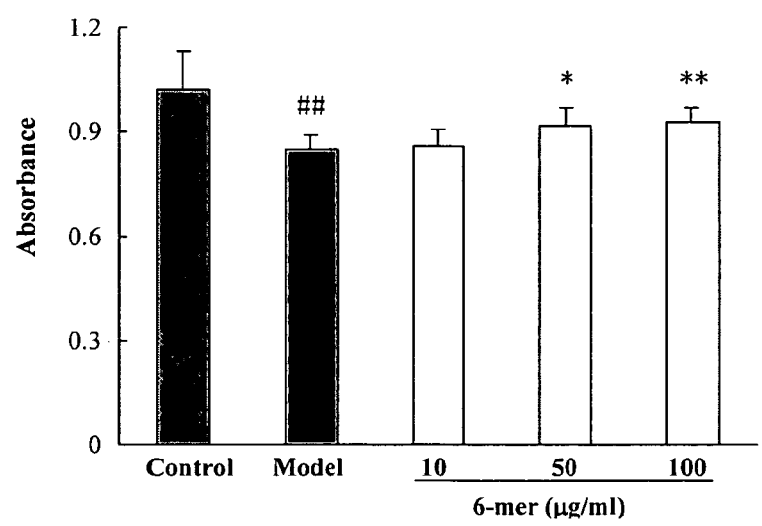
FIG. 12 shows the protective effects of the alginate oligosaccharide according to the present invention on NIT cells impaired by IAAP.
Figure 13:
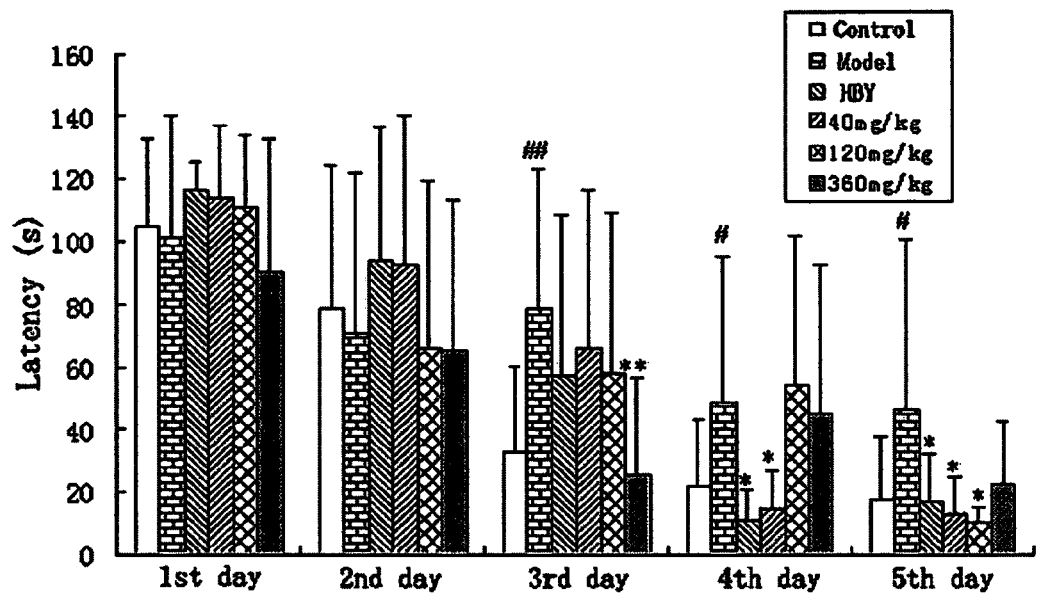
FIG. 13 shows the effect of the mixture of oxidative degradation product of the alginate oligosaccharide according to the present invention on the latency of AD mice induced by $A\beta_{1-40}$ tested with Morris water maze.
Figure 14:
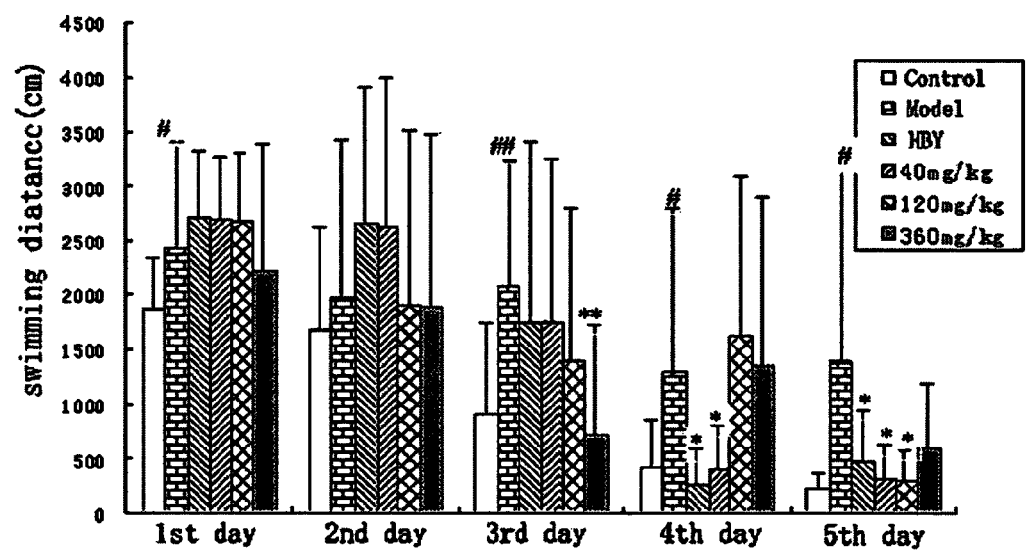
FIG. 14 shows the effect of the mixture of oxidative degradation product of the alginate oligosaccharide according to the present invention on the swimming distance of AD mice induced by $A\beta_{1-40}$ tested with Morris water maze.
Figure 15:
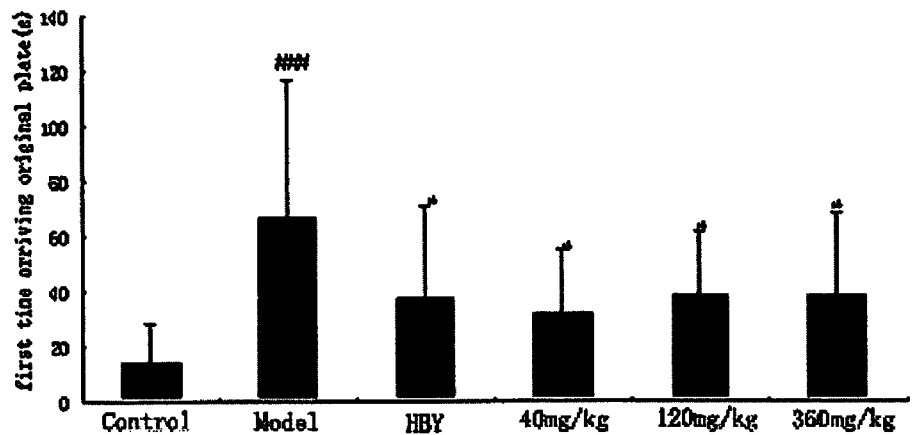
FIG. 15 shows the effect of the mixture of oxidative degradation product of the alginate oligosaccharide according to the present invention on the first time arriving the original plate of AD mice induced by $A\beta_{1-40}$ tested with Morris water maze.
Figure 16:
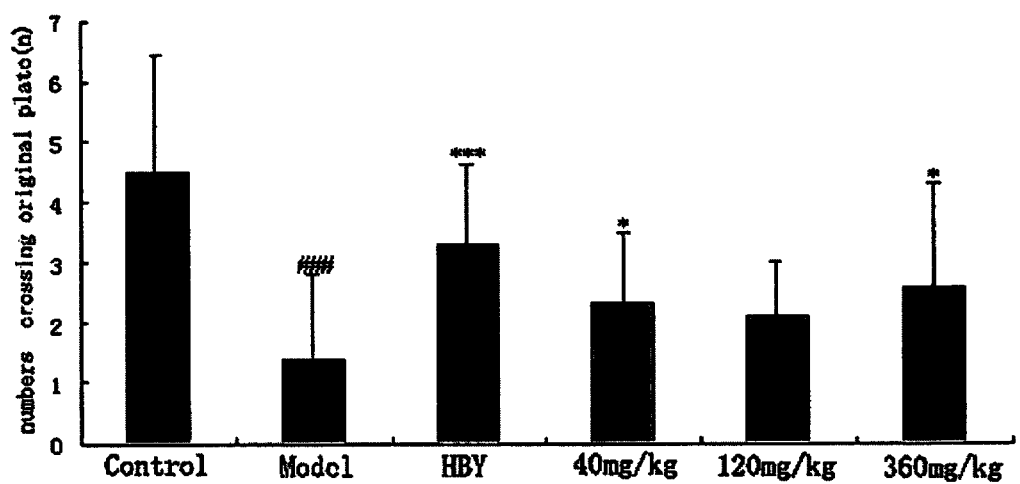
FIG. 16 shows the effect of the mixture of oxidative degradation product of the alginate oligosaccharide according to the present invention on the numbers crossing the original plate of AD mice induced by $A\beta_{1-40}$ tested with Morris water maze.

The results show that 6-mer could increase the survived cells impaired by amylin in a dose-dependent manner (FIG. 12). Each group has 6 animals. The data is shown as mean±SE. ## means statistical difference compared with the control group (p<0.01). * and ** means statistical difference compared with the IAPP treated group (p<0.05 and p<0.01). The data suggest that 6-mer has protective effects on pancreatic beta cells impaired with amylin 7.2 Effects of 6-mer on the Diabetic Mice Induced by Streptozotocin (STZ) In Vivo Sixty male NIH mice (weighed 18-22 g) are randomly divided to control, model, 50, 150, 450 mg/kg 6-mer-treated and 5 mg/kg dimethyldiguanide-treated groups. The mice are injected intraperitoneally with 150 mg/kg STZ except control group at the 1st day. Then the mice are given accordingly drugs consecutively for 10 days and eyeballs are picked out to extract blood on the $11^{th}$ day. The blood is taken to measure the glucose concentration. The concentration in each 6-mer-treated group is significantly lower than that in the model group, indicating that 6-mer has therapeutic effects on STZ-induced diabetic mice (table 13).

TABLE 13

Effects of 6-mer on the blood glucose concentration of diabetic mice induced by STZ ($\bar{x} \pm SD$)

| Group | Dose (mg/kg) | Number of mice | Blood glucose concentration (mg/dL) |
|---|---|---|---|
| Control | — | 10 | 150.6 ± 36.8 |
| Model | — | 10 | 312.4 ± 89.2### |
| 6-mer | 50 | 10 | 219.4 ± 67.8* |
|  | 150 | 10 | 179.6 ± 69.8** |
|  | 450 | 10 | 162.5 ± 3** |
| Dimethyldiguanide | 5 | 10 | 201.6 ± 58.9** | p < 0.05 vs control;
*P < 0.05,
**p < 0.01 vs model

Figure 17:
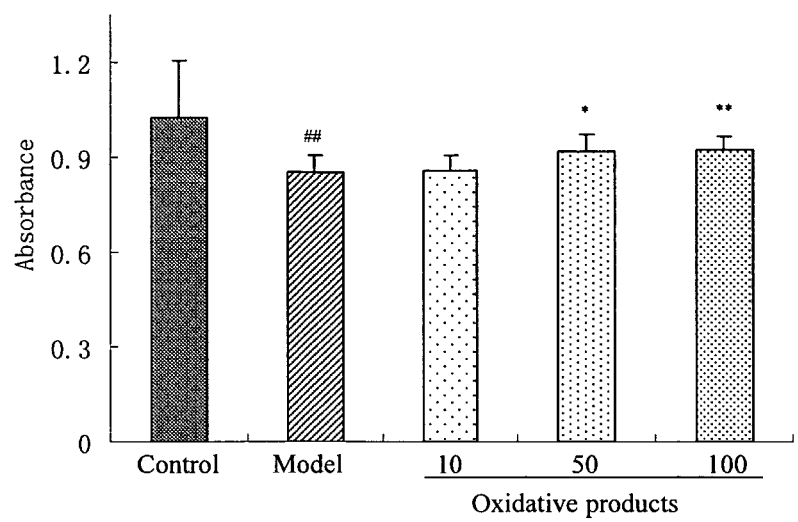
FIG. 17 shows the protective effects of the mixture of oxidative degradation product of the alginate oligosaccharide according to the present invention on NIT cells impaired by IAAP.

The same experiments are conducted with 2-mer to 22-mer alone or their mixture or the oxidative degradation products thereof. The results are similar to that of 6-mer to indicate their potential activity on AD and diabetes. FIGS. 13 to 16 show the behavioral results of the mixture of oxidative degradation products of the alginate oligosaccharides on AD mice induced by $A\beta_{1-40}$ injected to brain. Each group has 8 animals. The data are presented as mean±SE. The symbol # and ## stand for statistical difference compared with the control group (p<0.05, p<0.01), and * and ** stand for statistical difference compared with the model group (p<0.05, p<0.01). The data reveal that the mixture of the oxidative degradation products of the oligosaccharides can significantly improve the learning and memory ability of AD mice. FIG. 17 showed the protective results of the mixture of oxidative degradation products of the alginate oligosaccharides on pancreatic beta-cells cell line NIT impaired by IAAp (amylin). Each group has 6 animals. The data are presented as mean±SD. The symbol ## stands for statistical difference compared with the control group (p<0.01), and * and ** stand for statistical difference compared with the model group (p<0.05, p<0.01). The data reveal that the mixture of the oxidative degradation products of the alginate oligosaccharides has a significant preventive and curative effect on diabetes.

8 Statistic Analysis.

The data are statistically analyzed using software Statview expressed as mean±SE and compared by analysis of variance (ANOVA).

Based on the above results, the pharmaceutical composition containing an effective amount of the alginate oligosaccharides and pharmaceutically-acceptable carriers can be prepared. The said pharmaceutical composition includes an amyloid-β protein fibrils forming inhibitor and an islet amyloid protein fibrils forming inhibitor. The alginate oligosaccharide according to the present invention has important values in preparing drugs for prophylaxis and treatment of AD and diabetes.

We claim:

1. A composition consisting essentially of alginate oligosaccharide derivatives or their pharmaceutically-acceptable salts, wherein the alginate oligosaccharide derivatives are composed of β-D-mannuronic acid linked by 1,4 glycosidic bonds, wherein the reduced terminal in position 1 is carboxyl radical, as shown by the following formula II:

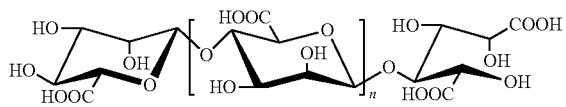

(II)

wherein, n represents 0 or an integer of 1 to 8.

2. The composition according to claim 1, wherein n is 2 to 8.

3. The composition according to claim 2, wherein n is 4 to 8.

4. A process for preparing alginate oligosaccharide derivatives or their pharmaceutically-acceptable salts, wherein the alginate oligosaccharide derivatives are composed of β-D-mannuronic acid linked by 1,4 glycosidic bonds, wherein the reduced terminal in position 1 is carboxyl radical, as shown by the following formula II:

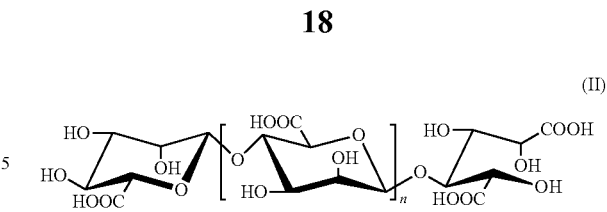

(II)

wherein, n represents 0 or an integer of 1 to 8, the process comprising the following steps in order:

acid hydrolysis step: an alginate aqueous solution is reacted for about 2 to 6 hrs in an autoclave at pH 2-6 and a temperature of about 100-120° C.;

pH-adjusting step: after the acid hydrolysis reaction is stopped, the value of pH is adjusted to about 7; and oxidative degradation step: an oxidant is added and reacted for 15 min to 2 hrs at a temperature of 100-120° C.

5. The process according to claim 4, wherein said alginate is sodium alginate and the acid hydrolysis reaction is carried out for 4 hrs under the condition of pH 4 and 110° C.

6. The process according to claim 4, wherein after adjusting the pH to about 7, alcohol is added to give a precipitate; the precipitate is filtered off with suction, dehydrated, dried and desalted.

7. The process according to claim 4, wherein the oxidant is copper hydroxide and the oxidative degradation is performed for 30 min at a temperature of 100° C.

8. A method for the treatment of Alzheimer's disease in a subject, comprising: administering, to the subject, a therapeutically effective amount of an active ingredient consisting essentially of mannuronic acid oligosaccharides represented by the following formula II,

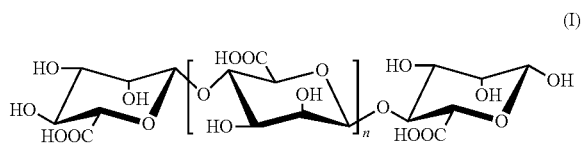

(I)

wherein, n represents 0 or an integer of 1 to 8.

9. A pharmaceutical composition, consisting essentially of:

i) an effective amount of mannuronic acid oligosaccharide derivatives represented by the following formula (II) for the prophylaxis and treatment of Alzheimer's disease or for the prophylaxis and treatment of diabetes;

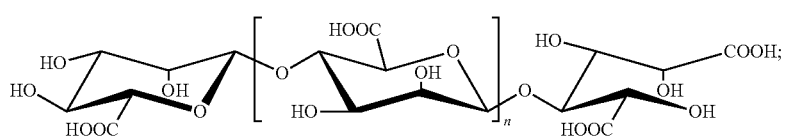

(II)

wherein, n represents 0 or an integer of 1 to 8.

and ii) a pharmaceutically-acceptable carrier.

10. The pharmaceutical composition according to claim 9, wherein the composition is any one selected from the group consisting of an amyloid-β protein fibrils forming inhibitor, an islet amyloid protein fibrils forming inhibitor and a fibrils disaggregating promoter.

* * * * *

UNITED STATES PATENT AND TRADEMARK OFFICE
CERTIFICATE OF CORRECTION

PATENT NO. : 8,835,403 B2  Page 1 of 1
APPLICATION NO. : 10/594100
DATED : September 16, 2014
INVENTOR(S) : Meiyu Geng et al.

It is certified that error appears in the above-identified patent and that said Letters Patent is hereby corrected as shown below:

In the Claims:

In claim 8, at column 15, lines 35-40, please replace formula I

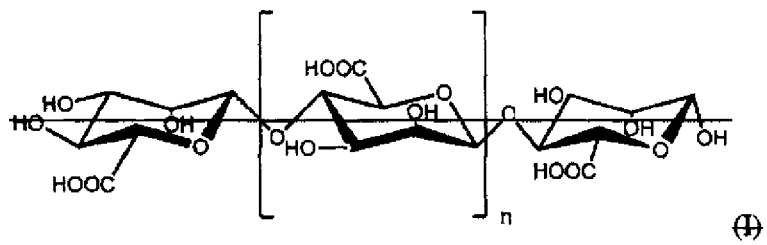

with formula (II)

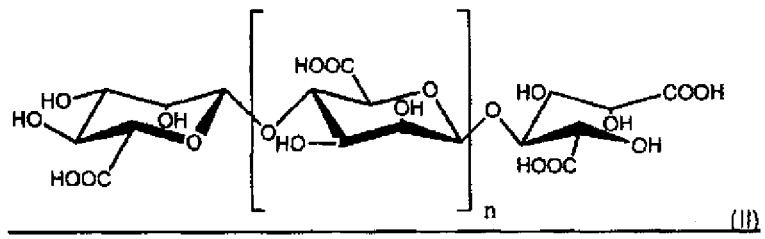

Signed and Sealed this
Seventeenth Day of March, 2015

Michelle K. Lee
*Director of the United States Patent and Trademark Office*